US00PP24491P3

(12) United States Plant Patent
Bacon

(10) Patent No.: US PP24,491 P3
(45) Date of Patent: May 27, 2014

(54) PEACH TREE NAMED 'SUPECHEIGHTEEN'

(50) Latin Name: *Prunus persica*
Varietal Denomination: Supecheighteen

(75) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 13/507,695

(22) Filed: Jul. 20, 2012

(65) Prior Publication Data

US 2014/0026265 P1 Jan. 23, 2014

(51) Int. Cl.
*A01H 5/00* (2006.01)

(52) U.S. Cl.
USPC ..... Plt./197

(58) Field of Classification Search
USPC ..... Plt./197
See application file for complete search history.

*Primary Examiner* — June Hwu
*Assistant Examiner* — Louanne Krawczewicz Myers
(74) *Attorney, Agent, or Firm* — Knobbe, Martens, Olson & Bear, LLP

(57) ABSTRACT

A new and distinct peach tree variety, *Prunus persica*, cv. 'Supecheighteen' is characterized by fruit with large size, early ripening, later blooming and early harvest.

1 Drawing Sheet

Latin name of the genus and species claimed: *Prunus persica.*

Variety denomination: 'Supecheighteen'.

BACKGROUND AND SUMMARY OF THE INVENTION

This invention relates to the discovery and asexual propagation of a new and distinct variety of peach, *Prunus persica* cv. 'Supecheighteen'. The new variety was first hybridized in February 2000 and selected in May 2002 by Terry Bacon as breeder number: 'PE133'. The new variety was first evaluated by Terry Bacon near Wasco, Calif. in Kern County. The variety 'Supecheighteen' was originated by hybridization.

The new variety 'Supecheighteen' is characterized by its large size, early ripening, later blooming and early harvest.

The seed parent is 'Supechthirteen' (the subject of U.S. Plant Pat. No. 13,142), and the pollen parent is from an unknown breeding selection. The parent varieties were first crossed in February 2000, with the date of sowing being February 2001, and the date of first flowering being February 2002. The new peach variety 'Supecheighteen' was first asexually propagated by Terry Bacon near Wasco, Kern County, Calif. in January 2007, by budding.

The new variety 'Supecheighteen' is distinguished from its seed parent, 'Supechthirteen', in that the new variety ripens about seventeen days later than 'Supechthirteen' and blooms ten days later. The fruit of the new variety 'Supecheighteen' is larger in diameter than that of 'Supechthirteen', at about 82 mm in comparison to 67 mm.

The new variety 'Supecheighteen' is not knowingly distinguished from that of its pollen parent, since the pollen parent was from an unknown breeding selection.

The new variety 'Supecheighteen' is similar in appearance to "Crimson Lady" (U.S. Plant Pat. No. 7,953) but it ripens about seven days earlier. The new variety 'Supecheighteen' ripens nearly with 'Maycrest' (U.S. Plant Pat. No. 4,064), but is larger in size at about 82 mm in comparison with 66 mm of 'Maycrest'.

The new variety 'Supecheighteen' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present peach variety. The illustration shows the upper and lower surfaces of the leaves, an exterior and sectional view of the fruit divided across the suture plane to show flesh color, pit cavity and the stone remaining in place. The photographic illustration was taken shortly after being picked.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 9 year old 'Supecheighteen' trees on Nemared (unpatented) rootstock, grown in the vicinity of Wasco, Kern County, Calif., during 2012, and is believed to apply to plants of the variety grown under similar conditions of soil and climate elsewhere.

TREE

General: (Measurements taken on 9 year old tree unless otherwise noted.).

*Size.*—Medium. Normal for most peach varieties. Reaches a height of approximately 3 meters including normal pruning.

*Spread.*—Normal for most peach varieties. Approximately 3 meters including normal pruning.

*Vigor.*—Moderately vigorous; growth of about 1.8 to about 2 meters high during the first growing season.

*Growth*.—Semi-upright.

*Productivity*.—Productive. Fruit set is usually two or more times desired amount for marketable size fruit; thinning and spacing of fruit is necessary.

*Form*.—Vase formed.

*Bearer*.—Regular.

*Fertility*.—Self-fertile.

*Canopy density*.—Dense.

*Hardiness*.—Hardy in all fruit growing areas of California; winter chilling requirement is approximately 350 hours at or below 7.2 C.

*Disease resistance/susceptibility*.—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.).

*Diameter*.—Approximately 20 cm, varies with soil type, fertility, climatic conditions and cultural practices.

*Texture*.—Medium shaggy, increases with age of tree.

*Trunk color*.—Outer bark about Light Greyed-green 197D to about Dark Greyed-green 197A; inner bark about Dark Greyed-orange 177A to about Medium Greyed-orange 174B.

Branches: (Measurements at approximately 90 cm above soil line.).

*Size*.—Diameter ranges from approximately 5 cm.

*Texture*.—Medium shaggy; increasing with tree age.

*Color*.—Branches vary from about Light Greyed-green 197D to about Medium Greyed-orange 166D.

*Number of lenticels*.—Medium.

*Lenticels density*.—Approximately 2-4 per $cm^2$.

*Lenticels color*.—About Medium Greyed-orange 166D.

*Lenticels size*.—Medium.

*Lenticels length*.—Approximately 3 mm.

*Lenticels width*.—Approximately 1.7 mm.

Flowering shoots: (Data taken in June at midpoint of current-season growth.).

*Size*.—Average diameter approximately 5 mm.

*Color*.—Topside: About Dark Greyed-orange 166B to Light Yellow-green 144C. Underside: About Light Yellow-green 144C.

*Internode length*.—Medium; approximately 10-15 cm. Midway on flowering shoot.

*Flowering shoot lenticels*.—Sparse. Color: About Light Greyed-green 196A. Diameter: Approximately 0.3 mm.

*Flowering shoot leaf buds*.—Shape: Elliptic to conical. Width: Approximately 3 mm. Length: Approximately 4 mm. Color: About Medium Greyed-green 197C.

*Flowering shoot flower buds*.—Shape: Conical. Width: Approximately 25 mm. Length: Approximately 4 mm. Color: About Medium Greyed-green 197C. Number of buds per node: Usually 2.

*Flower bud hardiness*.—Medium-hardy.

*Density of buds*.—Medium.

*Flower bud distribution*.—Generally isolated in groups of 2 on one year old shoots.

*Ratio of wood (leaf) buds to flowering shoots*.—½.

FOLIAGE

Leaves:

*Size*.—Medium.

*Average length*.—Medium; approximately 12-18 cm.

*Average width*.—Medium; approximately 3-4 cm.

*Thickness*.—Medium.

*Color*.—Upper Surface: About Medium Green 141A. Lower Surface: About Medium Green 139B.

*Form*.—Lanceolate.

*Tip*.—Cuspidate.

*Base*.—V-shaped.

*Margin*.—Crenate.

*Venation*.—Pinnately veined.

*Vein color*.—About Light Green 141D.

*Surface texture*.—Smooth.

*Leaf blade (ratio of length to width)*.—Medium; about 4/1.

*Shape in the cross section*.—Concave.

*Angle at apex*.—Medium.

*Profile*.—Up folded.

*Leaf blade tip*.—Curved downwardly.

*Angle of tip*.—Acute.

*Undulation of margin*.—Slight.

Petiole:

*Average length*.—Medium; approximately 8 mm.

*Average diameter*.—Approximately 2 mm.

*Color*.—About Light Green 141D.

Stipules:

*Number/leaf bud*.—Approximately 2.

*Typical length*.—Approximately 7 mm.

*Color*.—About Dark Greyed-orange 176A when dry.

*Persistence*.—Falls off.

Leaf glands:

*Form*.—Reniform.

*Average number*.—Between about 0 and 4; usually between about 2 and 4.

*Position*.—On petiole, alternate.

*Average size*.—Medium; approximately 1 by 1.5 mm.

*Color*.—About Medium Yellow-green 144B edges with corky middle about Medium Greyed-orange 173A.

FLOWERS

General:

*Flower blooming period*.—First Bloom: Approximately Feb. 15, 2012. Full Bloom: Approximately Feb. 18, 2012.

*Time of bloom*.—Early.

*Location of first bloom*.—Lower third of the canopy.

*Location of full bloom*.—Throughout the canopy.

*Duration of bloom*.—Medium; approximately 12 days.

*Type of bloom*.—Showy.

*Diameter of fully opened flower*.—Medium, approximately 40 mm.

*Flower aroma*.—Slight aroma.

*Shape*.—Rosaceous.

Peduncle:

*Length*.—Medium; approximately 4 mm.

*Diameter*.—Slender; approximately 1.5 mm.

*Color*.—About Medium Yellow-green 144A.

*Pubescence*.—Absent.

Petals:
*Number*.—5.
*Arrangement*.—Slightly overlapping.
*Length*.—Approximately 15 mm.
*Diameter*.—Approximately 9 mm.
*Shape*.—Oval.
*Apex shape*.—Rounded.
*Base shape*.—Narrows, cuneate.
*Color*.—Inner Surface: About Light Red-purple 62C, becoming darker over time. Outer Surface: About Light Red-purple 62C, becoming darker over time.
*Surface texture*.—Smooth.
*Margins*.—Slightly undulating.
*Frequency of flowers with double petals*.—Few to none.
*Petal size*.—Medium.
*Claw length*.—Short.
*Margin waviness*.—Weak.
*Base angle*.—Medium.
*Division of upper margin*.—Entire.
*Pubescence of inner surface*.—Absent.
*Pubescence of outer surface*.—Absent.

Sepals:
*Number*.—5.
*Length*.—Approximately 5 mm.
*Diameter*.—Approximately 3 mm.
*Shape*.—Triangular.
*Color*.—About Medium Red-purple 64B outside surface.
*Surface texture*.—Smooth.
*Margins*.—Entire.
*Positioning*.—Touching petals when opened.
*Pubescence of inner surface*.—Absent.
*Pubescence of outer surface*.—Absent.
*Frequency of flowers with double sepals*.—None.

Stamens:
*Number*.—Many; usually 38-48.
*Average length*.—Approximately 12 mm.
*Filament color*.—About Light Red-purple 62C, darkening to Medium Red-purple 64B as flower ages.
*Anther color*.—About Medium Red-purple 61B.
*Flower pollen color*.—About Dark Yellow-orange 22A when dried.
*Position*.—Perigynous.

Pistil:
*Number*.—Usually one.
*Average length*.—Approximately 18 mm.
*Ovary diameter*.—Approximately 1.5 mm.
*Pubescence*.—None.
*Stigma extension in comparison to anthers*.—Usually with and above.
*Frequency of supplementary pistils*.—Few.

Receptacle:
*Depth*.—Medium.
*Pubescence of inner surface* (*at pink bud stage*).—Absent.
*Pubescence of outer surface*.—Absent.

Ovary:
*Pubescence*.—Slight.
*Density of hairs*.—Dense.

FRUIT

General: (Description taken at firm-ripe on mature tree which obtained maximum quality under conditions stated in the description of the variety. Description taken on May 17, 2012 near Wasco, Kern County, Calif.).
*Harvest*.—
*Date of first pick*.—Approximately May 15, 2012.
*Date of last pick*.—Approximately May 18, 2012.
*Maturity when described*.—Firm-mature.
*Season ripening*.—Very early.
*Position of maximum diameter*.—Towards the middle.
*Symmetry about the suture*.—Somewhat symmetric.
*Size*.—Length (Stem End to Apex): Approximately 66 mm. Diameter in Line with Suture Plane: Approximately 66 mm.
*Diameter perpendicular to suture plane*.—Approximately 82 mm.
*Average weight*.—Approximately 200 gm.
*Form*.—Viewed from Apex: Rounded, nearly symmetrical. Viewed from Side, Facing Suture: Rounded, nearly symmetrical. Viewed from Side, Perpendicular to Suture: Rounded, nearly symmetrical.
*Apex shape*.—Rounded.
*Apex base*.—Rounded.

Fruit stem cavity:
*Shape*.—Rounded.
*Depth*.—Medium; approximately 0.8 cm.
*Breadth*.—Approximately 1.5 cm.
*Width*.—Medium.

Fruit stem:
*Length*.—Approximately 9 mm.
*Diameter*.—Approximately 2.5 mm.
*Color*.—About Medium Greyed-orange 164B.
*Adherence to stone*.—Medium.

Fruit skin:
*Thickness*.—Medium.
*Adherence to flesh*.—Strong.
*Surface texture*.—Medium.
*Pubescence*.—Medium.
*Ground color*.—About Dark Yellow-orange 17D when mature.
*Overcolor*.—About Medium Red 44A.
*Taste*.—Neutral.
*Reticulation*.—Absent.
*Roughness*.—Absent.
*Tenacity*.—Tenacious to flesh.
*Tendency to crack*.—None.

Flesh:
*Ripens*.—Evenly.
*Texture*.—Firm, non-melting.
*Fibers*.—Few.
*Flavor*.—Mild.
*Brix*.—Approximately 13°.
*Juice*.—Moderate.
*Aroma*.—Slight.
*Color*.—About Medium Yellow-orange 15C when mature.
*Anthocyanin*.—Expressed around stone only.
*Anthocyanin color of flesh*.—Weakly expressed.
*Anthocyanin color around stone*.—Present when fully mature.

*Amygdalin*.—Wanting.
*Acidity*.—Medium.
*Sugar content*.—Medium.
*Eating quality*.—Good.
*Stone/flesh ratio*.—About ¼.
*Firmness*.—Firm.

Shape of pistil point: Rounded.

Pit cavity size:

*Length*.—Approximately 26 mm.
*Diameter in line with suture plane*.—Approximately 32 mm.
*Diameter perpendicular to suture plane*.—Approximately 26 mm.
*Color*.—Red steaks at about Medium Red 44B.

Fruit use: Fresh market.

Fruit shipping and keeping quality: Good.

Suture line: Inconspicuous.

Stone:

*Stone freeness*.—Semi-free.
*Degree of adherence to flesh*.—Medium.
*Stone size*.—Medium. Size compared to Fruit: Medium. Length: Medium, approximately 35 mm. Diameter in Line with Suture plane: Approximately 28 mm. Diameter Perpendicular to Suture Plane: Approximately 22 mm. Width of Stalk End: Medium; approximately 5 mm. Angle of Stalk end: Right angle. Hilum: Oval.
*Stone form*.—Viewed from Side: Oval. Viewed from Ventral Side: Flattened.
*Stone shape*.—Base shape: Nearly straight. Apex shape: Pointed.
*Stone surface*.—Pitted throughout.
*Stone halves*.—Nearly symmetric.
*Stone ridges*.—Rounded continuous.
*Stone outgrowing keel*.—Partially developed.
*Stone tendency to split*.—Slight in wet season.
*Stone color*.—About Light Greyed-orange 165C to about Light Greyed-orange 165D when dried.
*Position of maximum*.—Toward middle.
*Sides*.—Nearly equal.
*Pits*.—Angular.
*Fibers*.—Short.
*Ventrical edge*.—Medium.
*Dorsal edge*.—Narrow grooves, interrupted.

What is claimed is:

1. A new and distinct peach tree as herein described and illustrated.

* * * * *

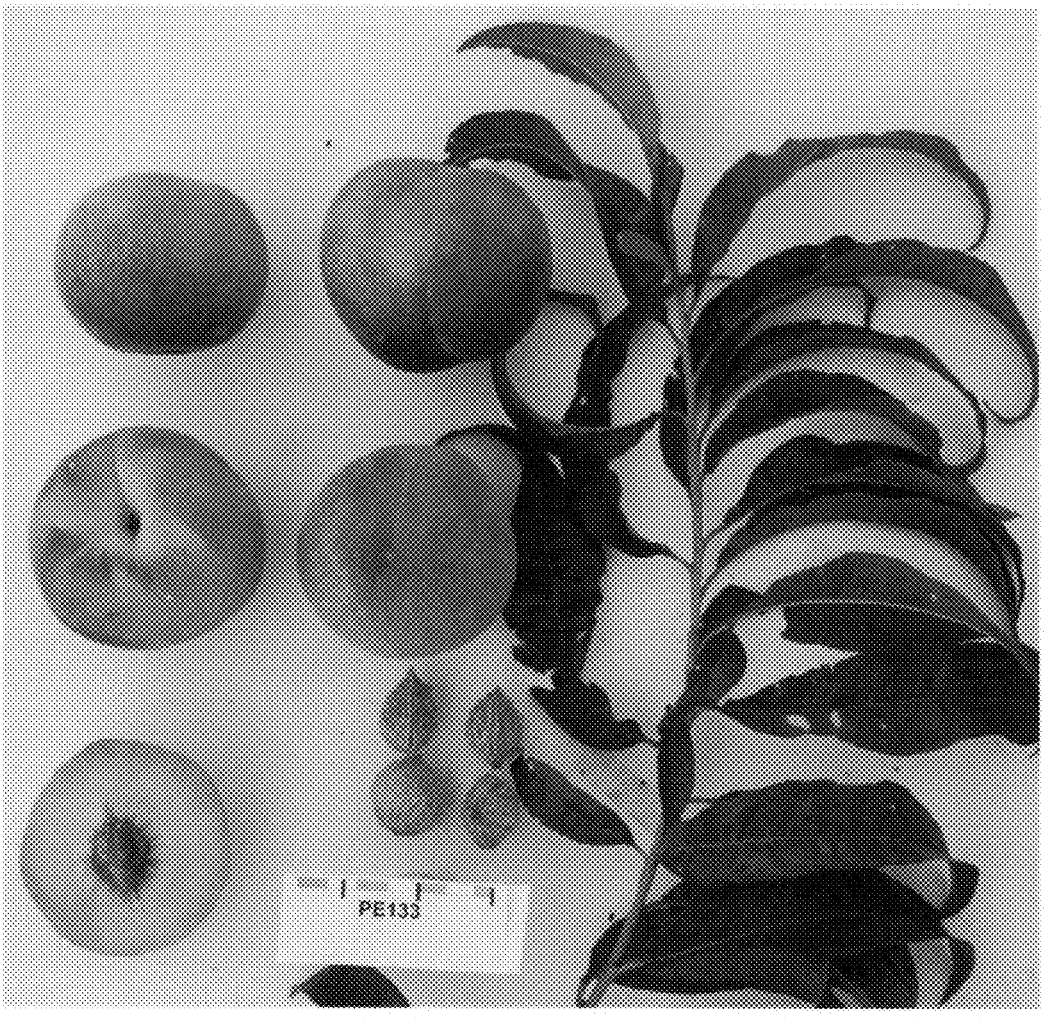
PE133